United States Patent [19]

Bernstein et al.

[11] 4,154,934
[45] May 15, 1979

[54] MERCAPTOACYLAMINO DERIVATIVES OF HETEROCYCLIC CARBOXYLIC ACIDS

[75] Inventors: Jack Bernstein; Kathryn A. Losee, both of New Brunswick, N.J.

[73] Assignee: E. R. Squibb & Sons, Inc., Princeton, N.J.

[21] Appl. No.: 933,009

[22] Filed: Aug. 11, 1978

[51] Int. Cl.² .................. C07D 211/98; C07D 207/50; C07D 205/04
[52] U.S. Cl. ..................................... 546/189; 546/244; 260/239 A; 260/326.25; 260/326.4; 424/244; 424/267; 424/274
[58] Field of Search ....................... 260/293.85, 293.63, 260/326.4, 326.25, 239 AR, 293.73

[56] References Cited
U.S. PATENT DOCUMENTS

| | | | |
|---|---|---|---|
| 4,046,889 | 9/1977 | Ondetti et al. | 260/239 AR |
| 4,052,511 | 10/1977 | Cushman et al. | 260/239 AR |
| 4,070,361 | 1/1978 | Petrillo | 260/293.85 |
| 4,086,338 | 4/1978 | Ondetti et al. | 260/239 AR |
| 4,091,024 | 5/1978 | Ondetti | 260/293.63 |
| 4,105,776 | 8/1978 | Ondetti et al. | 260/293.64 |

OTHER PUBLICATIONS

Shirota et al., "J. Med. Chem." vol. 20, pp. 1176–1181 (1977).

*Primary Examiner*—Natalie Trousof
*Assistant Examiner*—Robert T. Bond
*Attorney, Agent, or Firm*—Lawrence S. Levinson; Merle J. Smith

[57] ABSTRACT

New mercaptoacyl derivatives of heterocyclic carboxylic acids which have the general formula

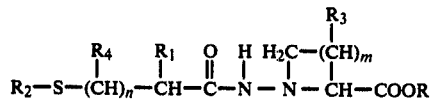

are useful as angiotensin converting enzyme inhibitors.

17 Claims, No Drawings

MERCAPTOACYLAMINO DERIVATIVES OF HETEROCYCLIC CARBOXYLIC ACIDS

SUMMARY OF THE INVENTION

This invention relates to new mercaptoacyl derivatives of heterocyclic carboxylic acids which have the general formula

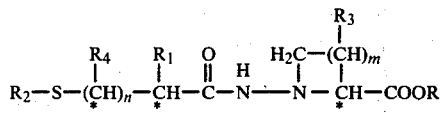

wherein R is hydrogen or lower alkyl;
$R_1$ and $R_4$ each is hydrogen, lower alkyl or phenyl-lower alkyl;
$R_2$ is hydrogen, $R_5$—CO or

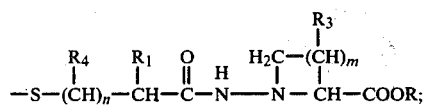

$R_3$ is hydrogen or hydroxy;
$R_5$ is lower alkyl, phenyl or phenyl-lower alkyl;
m is 1 to 3;
n is 0 or 1 and salts thereof.
The asterisks indicate asymmetric carbon atoms.

DETAILED DESCRIPTION OF THE INVENTION

The invention relates to mercaptoacyl derivatives of azetidine-2-carboxylic acid, proline and pipecolic acid and substituted analogs of those acids which have the structure in formula I above.

The lower alkyl groups represented by any of the variables include straight and branched chain hydrocarbon radicals from methyl to heptyl, for example, methyl, ethyl, propyl, isopropyl, butyl, isobutyl, t-butyl, pentyl, isopentyl and the like. The lower alkoxy groups are of the same kind having 1 to 7 carbons linked to oxygen, for example: methoxy, ethoxy, propoxy, isopropoxy, butoxy, isobutoxy and the like. The $C_1$–$C_4$ members, especially $C_1$ and $C_2$ members, of both types are preferred. The phenyl-lower alkyl groups are of a similar type, phenylmethyl being the preferred phenyl-lower alkyl group.

The lower alkanoyl groups and phenyl-lower alkanoyl groups $R_5$—CO are those including the acyl radicals of the lower ($C_2$–$C_7$) fatty acids, for example, acetyl, propionyl, butyryl, isobutyryl and the like. Similarly, those lower alkanoyl groups having up to four carbons, and especially acetyl, are preferred.

Broadly preferred are those compounds of formula I wherein R is hydrogen or lower alkyl; $R_1$ is hydrogen or lower alkyl; $R_2$ is hydrogen or $R_5$—CO; $R_3$ is hydrogen or hydroxy, especially hydrogen; $R_4$ is hydrogen; $R_5$ is lower alkyl, especially methyl, or phenyl; m is 2 or 3; and n is 0 or 1, especially 0. The hydroxy group, if present, is preferably on the pyrrolidine or piperidine ring and in the 3- or 4-position, especially the 3-position.

Especially preferred are the derivatives of proline which have the formula (II)

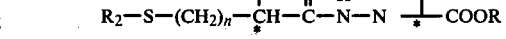

wherein R is hydrogen or lower alkyl;
$R_1$ is hydrogen or lower alkyl;
$R_2$ is hydrogen or $R_5$CO;
$R_3$ is hydrogen or hydroxy (preferably in the 3-position), especially hydrogen;
$R_5$ is lower alkyl or phenyl, especially the first, and most especially methyl; and
n is 0 or 1.
The stereoisomers in which the proline is in the L-form are especially preferred.

The new compounds of this invention are derived from nitrosoazetidine-2-carboxylic acid, nitrosoprolines or nitrosopipecolic acids which have the formula (III)

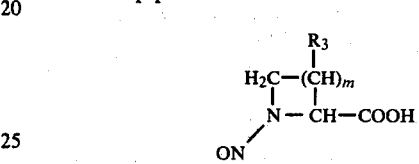

and which are prepared from the corresponding azetidine-2-carboxylic acid, proline or pipecolic acid, respectively, by means of nitrosyl tetrafluoroborate according to the method of Lijinsky et al., Tetrahedron, 1970, 26, 5137. They can also be produced by the method described by Nagasawa et al., J. Med. Chem. 16, 583 (1973).

The nitroso amino acid of formula III is next reduced to the N-amino derivative which has the formula (IV)

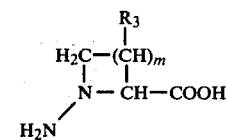

e.g., with zinc-acetic acid by the method described by Klosterman et al., Biochemistry 6, 173 (1967).

The amino derivative of formula IV is then acylated with an acyl halide which has the formula (V)

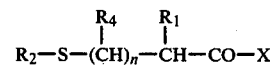

wherein $R_2$ is lower alkanoyl, benzoyl or phenyl-lower alkanoyl, and X is halogen, preferably chlorine or bromine, in an organic solvent inert to the reaction, like dimethylacetamide, dimethylformamide, etc., and in the presence of an acid acceptor, e.g., an organic base like N-methylmorpholine, N-ethylpiperidine, triethylamine, etc.

The product of this acylation reaction is a compound of formula I wherein R is lower alkanoyl, benzoyl or phenyl-lower alkanoyl. The corresponding product of formula I wherein $R_2$ is hydrogen can then be obtained by subjecting the acylated compound to ammonolysis, e.g., with alcoholic ammonia or aqueous ammonium hydroxide solution, or by hydrolysis with aqueous alkali, e.g., sodium hydroxide solution.

The acid product of formula I, i.e., wherein R is hydrogen, can be converted to the ester (wherein R is lower alkyl) by conventional esterification procedures, e.g., with a diazoalkane like diazomethane, 1-alkyl-3-p-tolyltriazene like 1-n-butyl-3-p-tolyltriazene or the like.

Compounds of formula I wherein $R_2$ forms symmetrical bis compounds are obtained by directly oxidizing with iodine the product of formula I wherein $R_2$ is hydrogen.

The products of this invention have one center of asymmetry in the heterocyclic ring and one or two more centers of asymmetry if $R_1$ and/or $R_4$ is other than hydrogen as indicated by the asterisks in formula I. These compounds accordingly exist in stereoisomeric forms or in racemic mixtures thereof. All of these are within the scope of the invention. The above described synthesis can utilize the racemate or one of the enantiomers as starting material. When the racemic starting material is used in the synthetic procedure, the stereoisomers obtained in the product can be separated by conventional chromatographic or fractional crystallization methods or by conversion to a salt with an optically active base, followed by fractional crystallization. In general, the L-isomer with respect to the carbon of the hetero ring constitutes the preferred isomeric form. The compounds of this invention, wherein R is hydrogen, form basic salts with various inorganic and organic bases which are also within the scope of the invention. Such salts include ammonium salts, alkali metal salts like sodium and potassium salts (which are preferred), alkaline earth metal salts like the calcium and magnesium salts, salts with organic bases, e.g., dicyclohexylamine, benzathine, N,N'-dibenzylethylenediamine, N-ethylpiperidine, N-methyl-D-glucamine, hydrabamine or alkylamine like triethylamine salts, salts with amino acids like arginine, lysine and the like. The non-toxic, physiologically acceptable salts are preferred, although other salts are also useful, e.g., in isolating or purifying the product.

The salts are formed in conventional manner be reacting the free acid form of the product with one or more equivalents of the appropriate base providing the desired cation in a solvent or medium in which the salt is insoluble, or in water and removing the water by freeze drying. The salts can be neutralized by conventional means to obtain the free acid.

Additional experimental details are found in the examples which are preferred embodiments and also serve as models for the preparation of other members of the group.

The compounds of this invention inhibit the conversion of the decapeptide angiotensin I to angiotensin II and therefore are useful in reducing or relieving angiotensin related hypertension. The compounds of this invention intervene in the angiotensinogen(renin)→angiotensin I→angiotensin II sequence by inhibiting angiotensin converting enzyme and reducing or eliminating the formation of the pressor substance angiotensin II. Thus by the administration of a composition containing one or a combination of compounds of formula I or physiologically acceptable salt thereof, hypertension in the species of mammal suffering therefrom is alleviated. A single dose, or preferably two to four divided daily doses, provided on a basis of about 0.1 to 100 mg. per kilogram per day, preferably about 1 to 50 mg. per kilogram per day is appropriate to reduce blood pressure as indicated in the animal model experiments described by S. L. Engel, T. R. Schaeffer, M. H. Waugh and B. Rubin, Proc. Soc. Exp. Biol. Med. 143 (1973). The substance is preferably administered orally, but parenteral routes such as subcutaneously, intramuscularly, intravenously or intraperitoneally can also be employed.

The compounds of this invention can be utilized to achieve the reduction of blood pressure by formulating in compositions such as tablets, capsules or elixirs for oral administration or in sterile solutions or suspensions for parenteral administration. About 10 to 500 mg. of a compound or mixture of compounds of formula I or physiologically acceptable salt is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which may be incorporated in tablets, capsules and the like are the following: a binder such as gum tragacanth, acacia, corn starch or gelatin; an excipient such as microcrystalline cellulose or dicalcium phosphate; a disintegrating agent such as corn starch, potato starch, alginic acid and the like; a lubricant such as magnesium stearate; a sweetening agent such as sucrose, lactose or saccharin; a flavoring agent such as peppermint, oil of wintergreen or cherry. When the dosage unit is a capsule, it may contain in addition to materials of the above type a liquid carrier such as a fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a vehicle such as water for injection, a naturally occurring vegetable oil like sesame oil, coconut oil, peanut oil, cottonseed oil, etc., or a synthetic fatty vehicle like ethyl oleate or the like. Buffers, preservatives, antioxidants and the like can be incorporated as required.

The following examples are illustrative of the invention and constitute especially preferred embodiments. All temperatures are in degrees Celsius.

EXAMPLE 1

(a) N-nitroso-L-proline

To a cooled suspension of 28.2 g. of nitrosyl tetrafluoroborate in 300 ml. of dry acetonitrile there is added, with vigorous stirring, over the course of 10 minutes, 18.4 g. of L-proline, followed by a solution of 19 g. of pyridine in 50 ml. of acetonitrile during 15 minutes. The stirring is continued for an hour and the reaction mixture is then concentrated to dryness under reduced pressure. The residue is extracted with 3×200 ml. of ethyl acetate, the ethyl acetate extracts are combined, washed twice with saturated sodium chloride solution that has been made slightly acidic with concentrated hydrochloric acid. The ethyl acetate solution is dried over anhydrous sodium sulfate, filtered and concentrated to dryness at room temperature under reduced pressure. The product, N-nitroso-L-proline metls at 108°–109° (dec.) after crystallization from a mixture of ether and petroleum ether (30°–60°).

(b) N-amino-L-proline

A solution of 10 g. of N-nitroso-L-proline in 500 ml. of 50% acetic acid is cooled in an ice bath and 40 g. of zinc dust is added gradually, with vigorous stirring, at a rate that the temperature of the reaction mixture is maintained below 10°. The addition requires about 15 minutes. The unreacted zinc dust is removed by filtration and the filtrate treated with hydrogen sulfide to precipitate the zinc as zinc sulfide. The precipitated zinc sulfide is removed by filtration and the filtrate evaporated to dryness. The residue is dissolved in 30 ml. of absolute ethanol and the solution allowed to remain overnight at 5°. The N-amino-L-proline, a yellow crystalline solid, is removed by filtration and melts at 153°–154° after drying.

(c) 1-[[3-(Acetylmercapto)-1-oxopropyl]amino]-L-proline

To a suspension of 3.9 g. of 1-amino-L-proline and 6.06 g. of N-methylmorpholine in 200 ml. of dimethylacetamide is added 4.98 g. of 3-acetylthiopropionyl chloride. The temperature of the reaction mixture rises to 34° spontaneously. The reaction mixture is then heated at 90° for 5 hours and allowed to cool to room temperature overnight. The crystalline solid, N-methylmorpholine hydrochloride, is removed by filtration and the filtrate concentrated under reduced pressure. The residue is dissolved in a minimum amount of 20% hydrochloric acid and the aqueous solution is then extracted with 3×150 ml. of ethyl acetate. The ethyl acetate extracts are combined, dried over anhydrous magnesium sulfate, and then concentrated under reduced pressure to yield the desired 1-[[3-(acetylmercapto)-1-oxopropyl]amino]-L-proline.

EXAMPLE 2

1-[(3-Mercapto-1-oxopropyl)amino]-L-proline

Nitrogen is bubbled into a solution of 12 ml. of concentrated aqueous ammonia in 25 ml. of water at 10° for 15 minutes. To this solution there is added 5.8 g. of 1-[(3-acetylmercapto)-1-oxopropyl]-L-proline and the resulting solution is stirred for 2½ hours under nitrogen. It is then cooled in an ice-bath and made strongly acidic with 20% hydrochloric acid. The mixture is extracted with 3×150 ml. of ethyl acetate, the ethyl acetate extracts are dried over anhydrous magnesium sulfate and then concentrated under reduced pressure. The oily residue is triturated with ether, the ether decanted and the last traces of ether removed under reduced pressure. The oily residue is dissolved in water and lyophilized to yield 1-[(3-mercapto-1-oxopropyl)amino]-L-proline hemihydrate as a viscous oil.

Analysis calcd. for $C_8H_{14}N_2O_3S \cdot 1/2\ H_2O$: C, 42.27; H, 6.65; N, 12.32; S, 14.11 Found: C, 42.59; H, 6.68; N, 12.29; S, 14.29

EXAMPLE 3

1-[(3-Mercapto-1-oxopropyl)amino]-L-azetidine-2-carboxylic acid

Following the procedures of Example 1 and Example 2, but substituting an equivalent amount of L-azetidine-2-carboxylic acid for the L-proline in Example 1, there is obtained 1-[(3-mercapto-1-oxopropyl)amino]-L-azetidine-2-carboxylic acid.

EXAMPLE 4

1-[(3-Mercapto-1-oxopropyl)amino]-L-proline, propyl ester

To a stirred suspension of 6.81 g. of 1-[(3-mercapto-1-oxopropyl)amino]-L-proline, hemihydrate in 50 ml. of ether, there is added dropwise a solution of 8.75 g. of 1-propyl-3-p-tolyltriazene in 100 ml. of ether and the mixture is heated to reflux for 4 hours. The reaction mixture is then cooled, filtered and extracted twice with 50 ml. portions of 5% hydrochloric acid and then with 50 ml. portions of 5% sodium bicarbonate solution. The ether solution is then washed with 100 ml. of saturated sodium chloride solution, dried over anhydrous magnesium sulfate and concentrated under reduced pressure to yield the crude product.

The product is purified by chromatography on a silica gel column.

EXAMPLE 5

1-[(3-Mercapto-1-oxopropyl)amino]-L-proline, sodium salt

To a solution of 4.54 g. of 1-[(3-mercapto-1-oxopropyl)amino]-L-proline hemihydrate in 150 ml. of water there is added 20 ml. of 1-N-sodium hydroxide solution and the resulting solution is lyophilized to yield the sodium salt of 1-[(3-mercapto-1-oxopropyl)amino]-L-proline.

EXAMPLE 6

N,N'-[Dithiobis(1-oxopropane-3,1-diyl)bis(1-amino-L-proline)]

To a solution of 3.0 g. of 1-[(3-mercapto-1-oxopropyl)amino]-L-proline hemihydrate in 100 ml. of water there is added sufficient 1N sodium hydroxide solution to adjust the pH to 6.5. To this solution, there is added dropwise, with vigorous stirring 27 ml. of 0.5M iodine solution (95% ethanol). The pH of the solution is maintained at 5.5 to 6.5 by the addition of 1N sodium hydroxide solution. Aqueous sodium thiosulfate is added to remove the excess iodine (color of iodine disappears). The solution is then concentrated under reduced pressure, acidified with concentrated hydrochloride acid and the precipitate is recovered by filtration. The precipitated product, N,N'-[dithiobis(3,1-diyl)bis(1-amino-proline)] is recrystallized from methyl alcohol.

EXAMPLE 7

1-[(2-Mercapto-1-oxoethyl)amino]-L-proline

Following the procedure of Example 1 and Example 2, but substituting an equivalent amount of acetylthioacetyl chloride for the 3-acetylthiopropanoyl chloride in Example 1, there is obtained 1-[(2-mercapto-1-oxoethyl)amino]-L-proline.

EXAMPLE 8

N,N'-[Dithiobis(1-oxopropane-3,1-diyl)bis(1-amino-L-azetidine-2-carboxylic acid)]

Following the procedure of Example 6, but substituting an equivalent amount of 1-[(3-mercapto-1-oxopropyl)amino]-L-azetidine-2-carboxylic acid for the 1-[(3-mercapto-1-oxopropyl)amino]-L-proline hemihydrate, there is obtained N,N-[dithiobis(1-oxopropane-3,1-diyl)bis(1-amino-L-azetidine-2-carboxylic acid)].

EXAMPLE 9

N,N'-[Dithiobis(1-oxopropane-3,1-diyl)bis(1-amino-L-pipecolic acid)]

Following the procedure of Example 6, but substituting an equivalent amount of 1-[(3-mercapto-1-oxopropyl)amino]-L-pipecolic acid for the 1-[(3-mercapto-1-oxopropyl)amino]-L-proline hemihydrate, there is obtained N,N'-[dithiobis(1-oxopropane-3,1-diyl)bis(1-amino-L-pipecolic acid)].

EXAMPLES 10 to 37

The following additional products of formula I having the substituents in the table below are obtained by the procedure of Examples 1 and/or 2 by substituting an equivalent amount of the starting material having the indicated substituents:

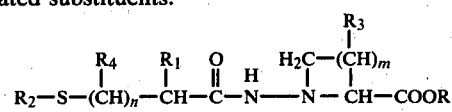

| Example | R | $R_1$ | $R_2$ | $R_3$ | $R_4$ | m | n |
|---|---|---|---|---|---|---|---|
| 10 | H | $CH_3$ | H | H | H | 2 | 1 |
| 11 | H | H | H | 3—OH | H | 2 | 0 |
| 12 | H | $CH_3$ | $CH_3CO$— | 3—OH | H | 2 | 1 |
| 13 | H | $CH_3$ | H | 3—OH | H | 2 | 1 |
| 14 | $C_2H_5$ | H | $CH_3CO$— | H | H | 2 | 1 |
| 15 | $C_4H_9$ | $CH_3$ | H | H | H | 2 | 1 |
| 16 | H | H | $C_2H_5CO$— | H | H | 2 | 0 |
| 17 | H | $C_2H_5$ | H | H | $C_2H_5$ | 2 | 1 |
| 18 | H | $CH_3$ | H | 3—OH | H | 2 | 0 |
| 19 | H | H | H | 4—OH | $CH_3$ | 2 | 0 |
| 20 | H | $CH_3$ | H | H | H | 2 | 0 |
| 21 | H | $C_6H_5CH_2$— | H | H | H | 2 | 0 |
| 22 | H | H | $C_6H_5CH_2CO$— | H | H | 2 | 1 |
| 23 | H | H | H | H | $C_6H_5CH_2CH_2$— | 2 | 1 |
| 24 | $CH_3$ | $C_2H_5$ | $C_6H_5CO$— | H | H | 2 | 1 |
| 25 | H | H | $CH_3CO$— | H | $C_6H_5CH_2$— | 2 | 0 |
| 26 | H | $CH_3$ | $CH_3CO$— | H | H | 3 | 1 |
| 27 | H | $CH_3$ | H | H | H | 3 | 1 |
| 28 | H | H | $CH_3CO$— | H | H | 3 | 0 |
| 29 | H | H | H | H | H | 3 | 0 |
| 30 | H | H | H | 3—OH | H | 3 | 1 |
| 31 | H | H | H | 4—OH | H | 3 | 1 |
| 32 | $C_3H_7$ | H | H | H | H | 3 | 1 |
| 33 | H | H | H | H | H | 3 | 0 |
| 34 | H | $CH_3$ | $CH_3CO$— | H | H | 1 | 1 |
| 35 | H | $CH_3$ | H | H | H | 1 | 1 |
| 36 | Na | H | H | H | H | 1 | 1 |
| 37 | H | H | $C_6H_5CO$ | H | H | 1 | 0 |

The L, D and DL forms of the foregoing products are produced by utilizing the L, D or DL form of the starting azetidine-2-carboxylic acid, proline or pipecolic acid, respectively.

What is claimed is:

1. A compound of the formula

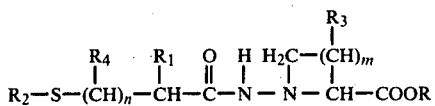

wherein
R is hydrogen or lower alkyl;
$R_1$ and $R_4$ each is hydrogen, lower alkyl or phenyl-lower alkyl;
$R_2$ is hydrogen, $R_5$—CO— or

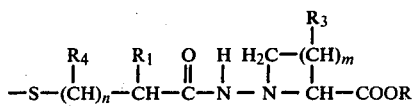

$R_3$ is hydrogen or hydroxy;
$R_5$ is lower alkyl, phenyl or phenyl-lower alkyl;
m is 1, 2 or 3;
n is 0 or 1; and salts thereof.

2. A compound as in claim 1 wherein m is 2.
3. A compound as in claim 1 wherein m is 1.
4. A compound as in claim 1 wherein m is 3.
5. A compound as in claim 1 wherein $R_3$ is hydrogen.
6. A compound as in claim 1 wherein $R_3$ is hydroxy.
7. A compound as in claim 1 wherein $R_2$ is hydrogen.
8. A compound as in claim 1 wherein n is 0.
9. A compound as in claim 1 wherein $R_2$ is

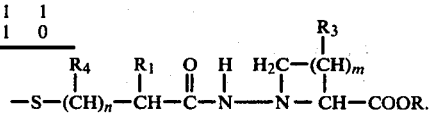

10. A compound as in claim 1 wherein R and $R_1$ each is hydrogen or lower alkyl; $R_2$ is hydrogen or $R_5$—CO; $R_3$ is hydrogen or hydroxy; $R_4$ is hydrogen; $R_5$ is lower alkyl or phenyl; m is 2 or 3; and n is 0 or 1.

11. A compound as in claim 2 wherein R, $R_2$ and $R_3$ each is hydrogen.

12. A compound as in claim 2 wherein R and $R_3$ each is hydrogen and $R_2$ is lower alkanoyl.

13. A compound as in claim 2 wherein R, $R_1$, $R_2$, $R_3$ and $R_4$ each is hydrogen and n is 1.

14. A compound as in claim 2 wherein R, $R_1$, $R_3$ and $R_4$ each is hydrogen, $R_2$ is acetyl and n is 1.

15. A compound as in claim 2 wherein R, $R_2$, $R_3$ and $R_4$ each is hydrogen and n is 1.

16. A compound as in claim 2 wherein R, $R_3$ and $R_4$ each is hydrogen; $R_2$ is acetyl and n is 1.

17. A compound as in claim 2 wherein R, $R_1$, $R_2$ and $R_3$ each is hydrogen and n is 0.

* * * * *